(12) United States Patent
Munk

(10) Patent No.: US 7,500,959 B2
(45) Date of Patent: Mar. 10, 2009

(54) MEDICATION DELIVERY SYSTEM WITH IMPROVED DOSE ACCURACY

(75) Inventor: Jens Aage Munk, Ølstykke (DK)

(73) Assignee: Novo Nordisk A/S, Bagsvaerd (DK)

( * ) Notice: Subject to any disclaimer, the term of this patent is extended or adjusted under 35 U.S.C. 154(b) by 636 days.

(21) Appl. No.: 09/972,828

(22) Filed: Oct. 4, 2001

(65) Prior Publication Data
US 2002/0107486 A1 Aug. 8, 2002

(30) Foreign Application Priority Data
Oct. 5, 2000 (DK) ................ 2000 01481

(51) Int. Cl.
*A61M 5/20* (2006.01)
(52) U.S. Cl. .................... 604/67; 604/154
(58) Field of Classification Search ............. 604/167, 604/155, 65–67, 135, 134, 133, 132, 131, 604/151–154, 121, 14; 128/DIG. 12, DIG. 13, 128/DIG. 1
See application file for complete search history.

(56) References Cited

U.S. PATENT DOCUMENTS

| | | | |
|---|---|---|---|
| 3,555,254 A | 1/1971 | Gerber | 235/151 |
| 4,291,692 A | 9/1981 | Bowman et al. | 128/214 |
| 4,373,535 A * | 2/1983 | Martell | 600/578 |

(Continued)

FOREIGN PATENT DOCUMENTS

CA 1278481 1/1991

(Continued)

OTHER PUBLICATIONS

English language abstract of JP 5-297117.

(Continued)

*Primary Examiner*—Nicholas D. Lucchesi
*Assistant Examiner*—Aarti Bhatia
(74) *Attorney, Agent, or Firm*—Wesley A. Nicolas; Marc A. Began

(57) ABSTRACT

The invention relates to: A medication delivery device (1) for delivering a specific dose comprising a medication cartridge (11) having an outlet (111) and a piston (112), and means (12) for holding said cartridge, and a piston rod (13) being operable to engage and displace said piston, and electrically driven actuating means (15), and driving means (161, 162) for transferring movement from said actuating means to said piston rod, and memory means (17) for storing data, and processing means (18) for evaluating said data and for controlling said actuating means. The object of the present invention is to provide a medication delivery system that combines a relatively high dose accuracy with the use of relatively low quality mechanical components and which enables compensation for built-in non-linearities. The problem is solved in that a first set of data (19) describing the actual movement (130) of said piston rod (13) relative to said medication cartridge (11) as a function of the movement (150) of said actuating means (15) is stored in said memory means (17), and the movement (130) of the piston rod (13) governing the delivered dose is controlled by the processing means (18) on the basis of said first set of data (19). This has the advantage of allowing compensation for mechanical inaccuracies and built-in non-linearities linearities. The invention may e.g. be used in injection or infusion devices for a person's self-treatment of a disease such as diabetes.

11 Claims, 5 Drawing Sheets

U.S. PATENT DOCUMENTS

| | | | | |
|---|---|---|---|---|
| 4,466,426 | A | * 8/1984 | Blackman | 604/187 |
| 4,493,704 | A | * 1/1985 | Beard et al. | 604/154 |
| 4,529,401 | A | 7/1985 | Leslie et al. | 604/131 |
| 4,557,726 | A | 12/1985 | Reinicke | 604/67 |
| 4,620,848 | A | 11/1986 | Sutherland et al. | 604/154 |
| 4,662,872 | A | 5/1987 | Cane | 604/151 |
| 4,685,903 | A | * 8/1987 | Cable et al. | 604/154 |
| 4,741,736 | A | 5/1988 | Brown | 604/134 |
| 4,846,797 | A | * 7/1989 | Howson et al. | 604/154 |
| 4,919,596 | A | 4/1990 | Slate et al. | 417/18 |
| 4,943,279 | A | * 7/1990 | Samiotes et al. | 604/151 |
| 4,950,246 | A | 8/1990 | Muller | |
| 4,952,205 | A | 8/1990 | Mauerer et al. | |
| 5,034,004 | A | * 7/1991 | Crankshaw | 604/154 |
| 5,176,502 | A | 1/1993 | Sanderson et al. | 417/18 |
| 5,190,522 | A | 3/1993 | Wojcicki et al. | 604/65 |
| 5,197,322 | A | 3/1993 | Indravudh | 73/3 |
| 5,211,626 | A | 5/1993 | Frank et al. | 604/65 |
| 5,261,882 | A | * 11/1993 | Sealfon | 604/135 |
| 5,295,967 | A | * 3/1994 | Rondelet et al. | 604/154 |
| 5,588,963 | A | 12/1996 | Roelofs | 604/65 |
| 5,628,309 | A | * 5/1997 | Brown | 600/310 |
| 5,637,095 | A | * 6/1997 | Nason et al. | 604/135 |
| 5,647,853 | A | * 7/1997 | Feldmann et al. | 604/155 |
| 5,651,775 | A | * 7/1997 | Walker et al. | 604/207 |
| 5,681,285 | A | * 10/1997 | Ford et al. | 604/151 |
| 5,695,464 | A | * 12/1997 | Viallet | 604/67 |
| 5,925,022 | A | * 7/1999 | Battiato et al. | 604/208 |
| 5,951,510 | A | 9/1999 | Barak | 604/67 |
| 6,302,869 | B1 | 10/2001 | Klitgaard | |
| 6,537,251 | B2 | * 3/2003 | Klitmose | 604/135 |

FOREIGN PATENT DOCUMENTS

| | | |
|---|---|---|
| DE | 3824217 | 1/1990 |
| DE | 196 43 813 | 4/1998 |
| DE | 19643813 | 4/1998 |
| DE | 19742632 | 4/1999 |
| DE | 10020494 | 11/2000 |
| EP | 561123 | 1/1993 |
| EP | 0 561 123 | 9/1993 |
| FR | 853259 | 3/1940 |
| GB | 2146460 | 4/1985 |
| GB | 2311866 | 10/1997 |
| JP | 61-280868 | 12/1986 |
| JP | 63-257574 | 10/1988 |
| JP | 4-129568 | 4/1992 |
| JP | 5-297117 | 12/1998 |
| WO | WO 99/58178 | 5/1999 |
| WO | 99/52575 | 10/1999 |
| WO | WO 99/58178 | 11/1999 |

OTHER PUBLICATIONS

English language abstract of JP 4-1294568 from Patent Abstracts of Japan.

English language abstract of JP 2000-513974 from esp@cenet.

* cited by examiner

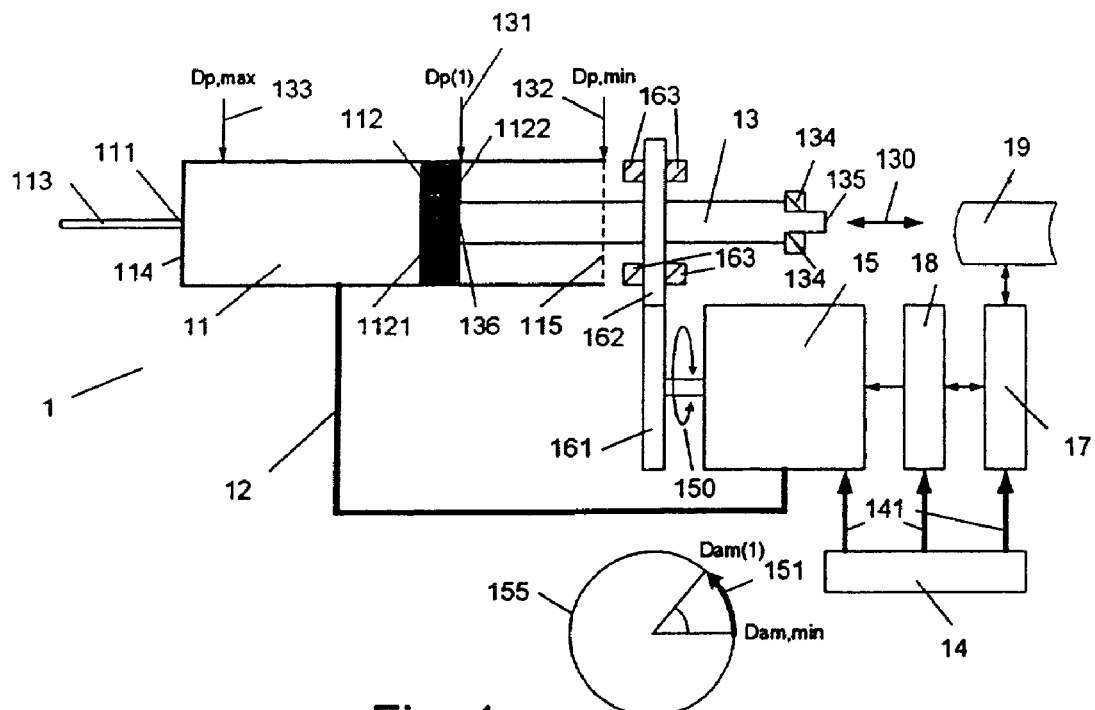
Fig. 1.a
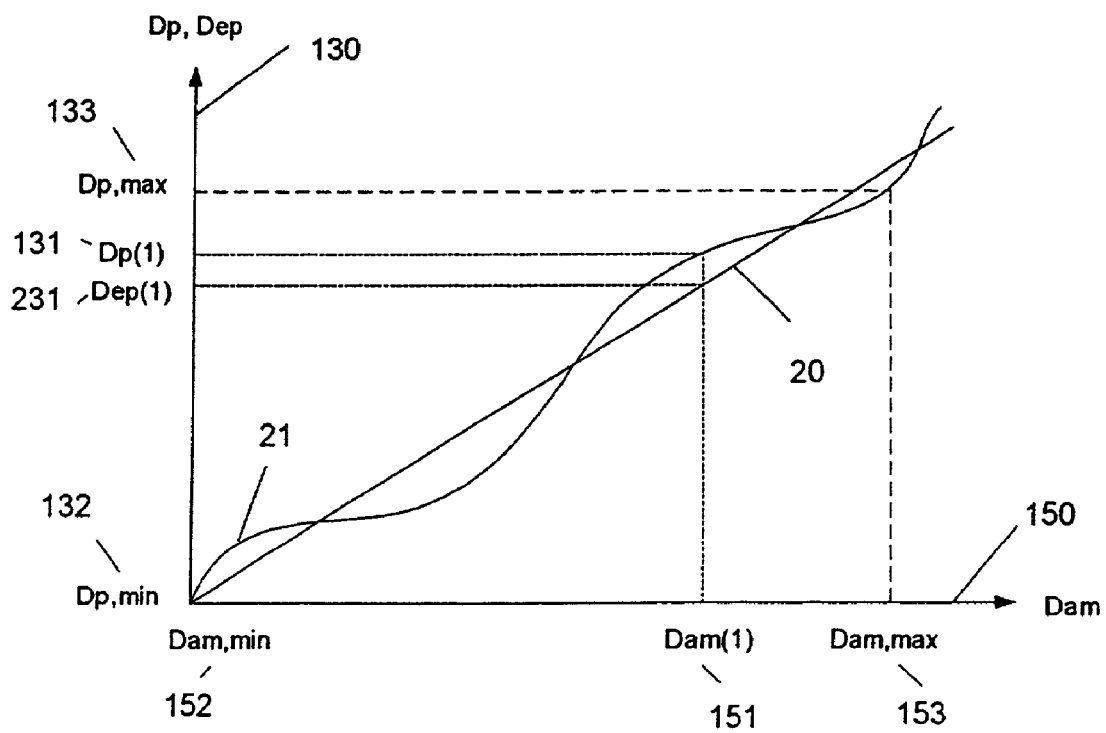
Fig. 1.b

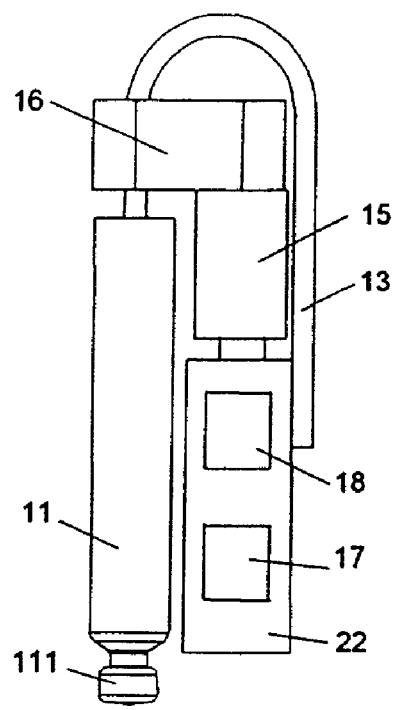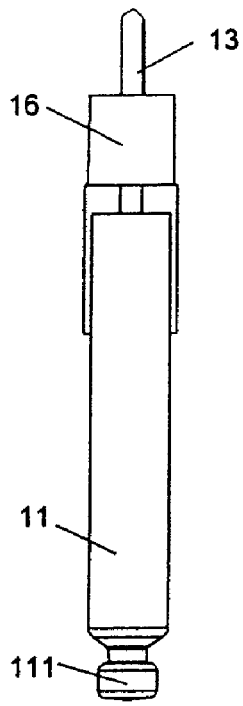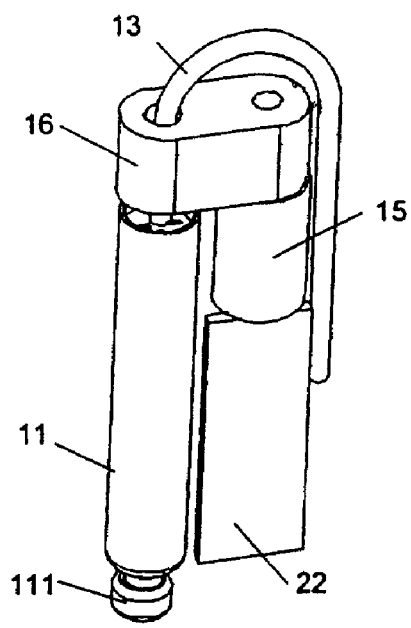
Fig. 2.a	Fig. 2.b	Fig. 2.c

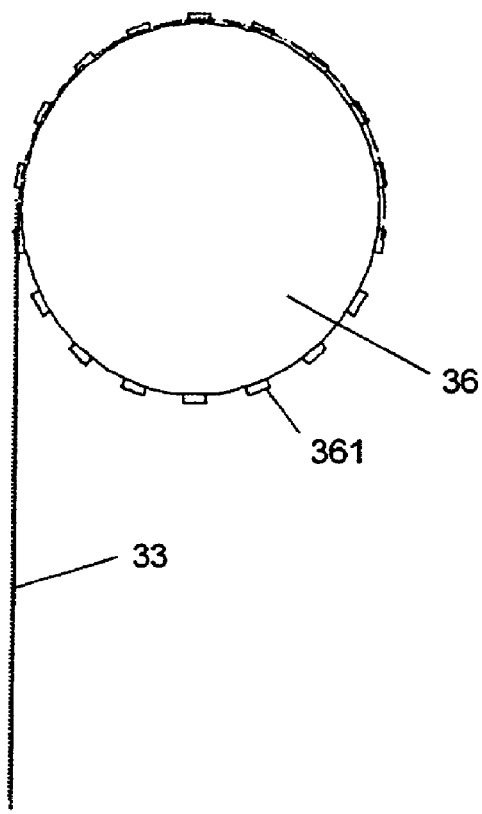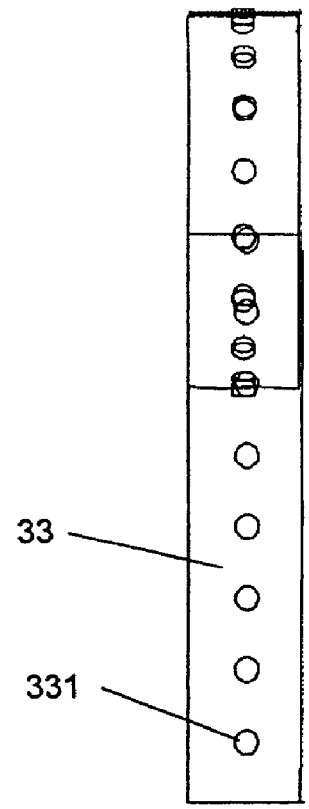
Fig. 3.a
Fig. 3.b
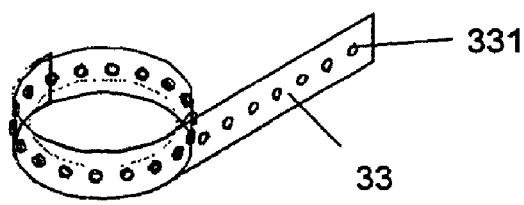
Fig. 3.c

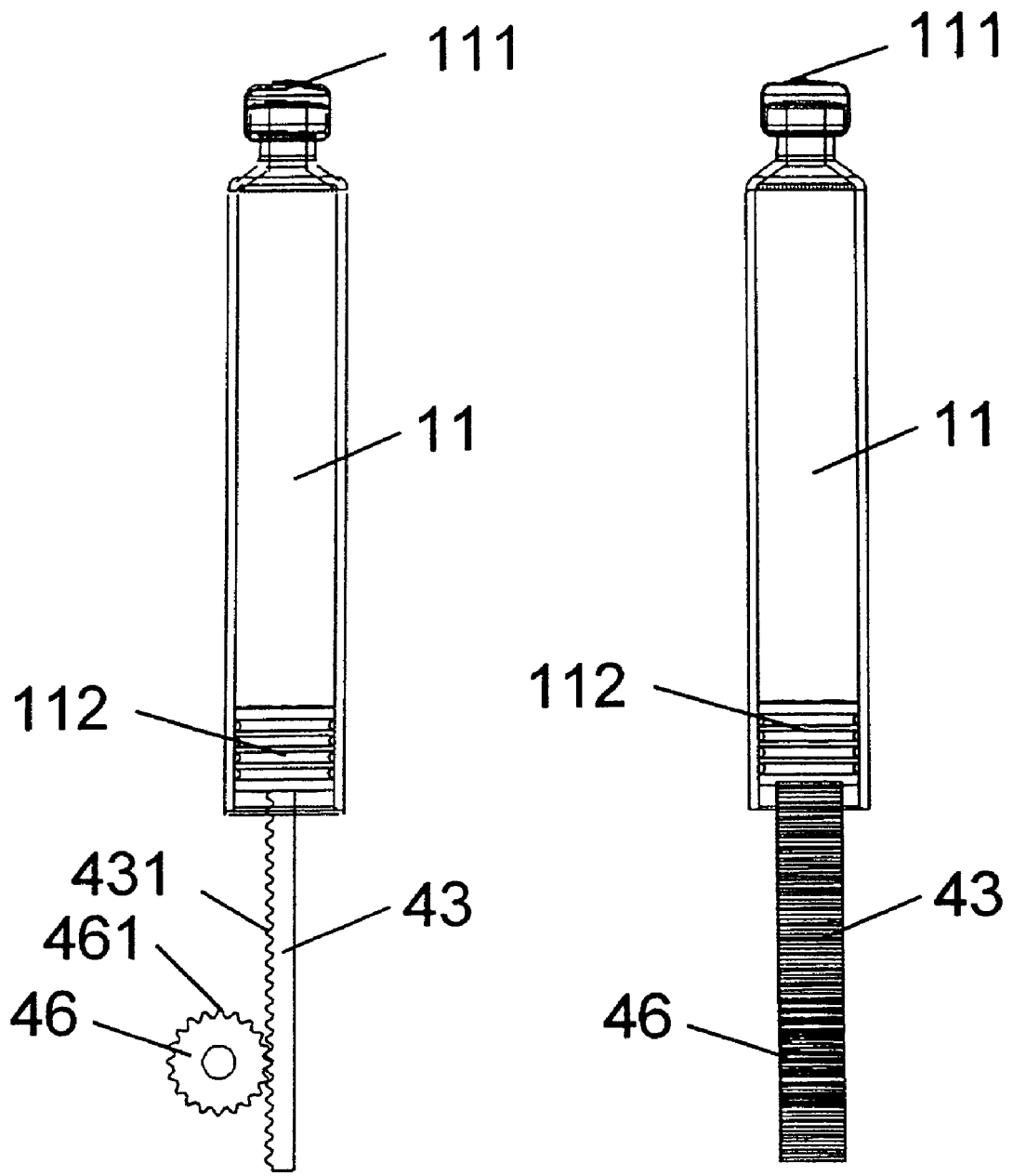
Fig. 4.a    Fig. 4.b

MEDICATION DELIVERY SYSTEM WITH IMPROVED DOSE ACCURACY

THE TECHNICAL FIELD OF THE INVENTION

The invention relates to the design of medication delivery systems with a view to dose accuracy and production cost.

The invention relates specifically to: A medication delivery device for delivering a specific dose comprising a medication cartridge having an outlet and a piston, and means for holding said cartridge, and a piston rod being operable to engage and displace said piston, and electrically driven actuating means, and driving means for transferring movement from said actuating means to said piston rod, and memory means for storing data, and processing means for evaluating said data and for controlling said actuating means.

DESCRIPTION OF RELATED ART

The following account of the prior art relates to one of the areas of application of the present invention, medication delivery systems for self-treatment of a disease.

In a medication delivery system for self-treatment of a disease such as diabetes, safety in the handling of the injection or inhalation is of major importance. Various systems having built-in electronic processing means and driving means for controlling the delivery process have been described.

U.S. Pat. No. 4,950,246 describes e.g. an injection pen including an electromotor, which is controlled by an electronic control unit (e.g. a processor) comprising i.a. memory means for storing data relating to the medication delivery process (e.g. reservoir stock status, number of units of injection fluid to be delivered to the user-patient, etc.) and comparator means for comparing number of units of injection fluid with reservoir stock status.

The 'on board' electronic processing means allows various checks and controls related to the correct handling of the medication to be implemented. One parameter that is of special importance is dose accuracy. It is important to accurately control the dose given at a particular instance. However, the accuracy with which a dose may be given is limited by the sum of the inaccuracies incurred by the various elements in the dosing process, including non-linearities in the volume of the cartridge holding the medication and non-linearities in the movement of the piston, the latter being governed by properties of the piston, the piston rod, the driving means and the actuating means and their mutual cooperation. An improvement in dose accuracy from a given level may be achieved by reducing the above-mentioned non-linearities, e.g. by reducing the faults in a threaded piston rod driven by a nut by providing a rod that is less skew and has an improved accuracy of the thread. Such an improvement comes, however, at a cost and may require the use of special materials limiting the freedom of design and possibly increasing cost.

From the field of numerically controlled machines it is known to accomplish an improvement in the accuracy with which a positioning device such as a plotter or machine tool may position a driven part by providing a system for overcoming the repeatable mechanical errors present in such a device. U.S. Pat. No. 3,555,254 discloses e.g. a method for reducing errors in a device for positioning a driven part relative to a reference member and including a computer for converting input commands into output commands having arguments related to the positions to which said driven part is to be moved, said method comprising the steps of storing a table of error values versus reference positions in a memory device associated with said computer, and thereafter operating said computer in accordance with such a program.

DISCLOSURE OF THE INVENTION

The problem of the prior art is that an improvement of dose accuracy in a medication delivery system requires the use of higher quality components limiting the choice of materials and increasing costs.

The object of the present invention is to provide a medication delivery system that combines a relatively high dose accuracy with the use of relatively low quality mechanical components, and which enables compensation for built-in non-linearities.

This is achieved according to the invention in that a first set of data describing the actual movement of said piston rod relative to said medication cartridge as a function of the movement of said actuating means is stored in said memory means, and the movement of the piston rod governing the delivered dose is controlled by the processing means on the basis of said first set of data.

A description of the actual movement of the piston rod relative to the medication cartridge involves knowledge of the functional dependence f between the movement $D_{am}$ of the actuating means and the actual displacement $D_p$ of the piston rod, $D_p=f(D_{am})$, the latter primarily deciding an actually delivered dose $V_d=g(D_p)=h(D_{am})$ for a given geometry of the medication cartridge. The functional dependence should in general be known over the range $D_{am} \in [D_{am, min}, D_{am, max}]$, i.e. the range of movement of the actuating means corresponding to the range of operation of the piston rod $[D_{p, min}, D_{p, max}]$. The movement of the actuating means could e.g. be the rotation of a motor through a certain number of turns or fractions of a turn, in which case $D_{am}$ would represent the relevant rational number of turns, e.g. 1.73 turn. If e.g. the relationship between the movement of the actuating means and the actual displacement of the piston rod is non-linear, but cyclical and known, only data governing a single cycle is needed, though.

In the present context, the term 'a first set of data' in connection with 'the dependence between the movement $D_{am}$ of the actuating means and the actual displacement $D_p$ of the piston rod' is taken to mean a set of corresponding isolated values over a range or alternatively an algebraic expression ('a formula') valid in a range.

In the present context, the term 'medication delivery system' is taken to mean an injector type device (such as a pen injector or a jet injector) for delivering a discrete dose of a liquid medication (possibly in the form of small drops) or a medication pump for continuous delivery of a liquid medication-in both cases in combination with relevant electronic monitoring and control and possibly communications units.

In the present context the term 'piston' is taken to mean a displaceable plate or cylinder that fits tightly against the inner walls of a cartridge. A surface of the piston that faces the inner part of the cartridge and which may be brought into contact with the contents of the cartridge is termed 'the inner surface of the piston', and the opposite side of the piston is termed 'the outer surface of the piston'. In cooperation with a 'piston rod' that is engaged with 'the outer surface of the piston', the 'piston' may be displaced and used to apply pressure to a surface of the contents of the cartridge being in contact with 'the inner surface of the piston', thus e.g. delivering a dose through the outlet of the cartridge, if the piston is displaced in the direction towards the outlet. In the present context, the term 'piston' may also apply to a movable wall or membrane that engages with a plunger, which is an integral part of the piston rod.

An advantage of the invention is that the piston rod (and other components having an influence on dose accuracy) may be made with a lower tolerance than otherwise because the non-linearity in the displacement of the rod over the operating range of the piston is handled by using a lookup table of corresponding values of expected and actual 'coordinates' (or an algebraic expression between them if the non-linearity is predictable) for the position of the piston relative to the cartridge allowing a correction to be made. The non-linearity in the displacement of the rod over the operating range of the piston may have various origins. It may e.g. be due to faults in the rod including that the rod is skew, and to in-homogeneities in the (ideally) regularly spaced driving means (e.g. thread) on the rod that, together with corresponding cooperating driving means (e.g. nut and/or gear wheel) that cooperate with the actuating means, form the basis for the movement transferred from the actuating means to the rod. The non-linearity in the displacement of the rod over the operating range may, however, also be of a more 'predictable' origin, e.g. in the form of 'designed in' non-linearities (e.g. the cyclical non-linearities of a straight toothed rod being driven by a gear wheel). The relation between corresponding values of expected and actual 'coordinates' of the displacement may (if necessary) be obtained in a calibration process prior to the use of the device in question. In some cases, a mathematical relation between the corresponding values of 'expected' and actual 'coordinates' of the displacement exists, and this relation may be used by the processing means to predict the actual displacement of the piston rod as a function of the movement of the actuating means, thus making a preceding calibration superfluous.

The use of a medication delivery system according to the invention may be driven by either a need for an improved dose accuracy with a given quality of components or by a need or wish to lower the costs by using lower quality components, while maintaining the same dose accuracy. A need for an improved dose accuracy may e.g. come from the use of medication with a higher concentration of the active elements than previously.

When said first set of data comprises a relationship between corresponding values of actual delivered dose and the movement of said actuating means, it is ensured that an intended dose, e.g. in the form of a user input, may be directly translated by the processing means to a specific movement of the actuating means.

When said first set of data comprises corresponding values of the expected and the actual position of the piston relative to the medication cartridge and the position of the actuating means, it is ensured that a compensation for a non-linearity (be it stochastic or periodic and unintentional or built-in) may be controlled by the processing means.

When said first set of data comprises a mathematical relationship between the corresponding values, said relationship being executable by said processing means, it is ensured that the processing means can manage a compensation for non-linearities described by the mathematical relationship in question. Such a relationship could have its origin in the mechanical design of the piston rod, the driving means, etc.

When said first set of data is based on a prerecorded calibration of the medication delivery device and said calibration data are stored in said memory means, it is ensured that any non-linearities, including stochastically distributed ones (such as e.g. certain mechanical inaccuracies) and built-in ones may be compensated for.

When the medication cartridge is replaceable, it is ensured that the major part of the medication device may be used again and again only by inserting a new cartridge (and possibly a new needle in the case of an injection device) when the contents of the medication cartridge has been ejected or when another medication is to be used, i.e. e.g. in the situation of a person's self-treatment of a disease (e.g. diabetes) that requires frequent delivery of medication (e.g. insulin) over an extended period of time. If the replaceable cartridge contains a fully functioning piston (and possibly a corresponding piston rod), a convenient and flexible solution is provided, where the medication cartridge may be replaced in a quick and hygienically safe way.

When the piston rod is made of a salient material, it is ensured that an improved flexibility in the physical design of the medication delivery system is introduced.

When the piston rod describes a curved path, a greater degree of freedom in the design of the medication delivery device may be provided. An advantage of this is that a more compact construction may be achieved, using e.g. a 180 degrees curve of the path of the piston rod.

When the piston rod is composed of cooperating identical elements in a chain-like construction, it is ensured that a very compact construction may be provided.

When the piston rod is formed as a tape, it is ensured that a simple, potentially economical and compact solution is provided.

In the present context the term 'tape formed' in connection with 'piston rod' is taken to mean that the cross-section of the rod perpendicular to its longitudinal direction is 'wider' than its 'height'. It does not have to take the form of a rectangular cross-section, but could be grooved or toothed or wave-formed or convex or concave or something else that might be convenient from a design point of view.

Our co-pending patent application "Medication delivery device with bended piston rod" discloses various embodiment of a tape-shaped piston rod and is incorporated in the present application by reference.

When the piston rod is made of a plastics material, it is ensured that an economical and light-weight solution that is well suited for production in larger quantities is provided.

When the piston rod is covered with a plastics material, it is ensured that a solution combining the benefits of using a plastics material (e.g. corrosion resistance) with those of other materials (e.g. greater mechanical stability, stiffness, etc.) is provided.

BRIEF DESCRIPTION OF THE DRAWINGS

The invention will be explained more fully below in connection with a preferred embodiment and with reference to the drawings, in which:

FIGS. 1.a and 1.b illustrate the basic principles of a medication delivery system according to the invention, FIGS. 2.a-2.c show a possible appearance of a medication delivery system (without a housing) according to the invention, FIGS. 3.a-3.c show a tape-shaped piston rod and corresponding driving means according to the invention for which periodic as well as stochastic non-linearities may be present, FIGS. 4.a and 4.b show a toothed piston rod and corresponding driving means according to the invention for which periodic as well as stochastic non-linearities may be present.

Figure 5:
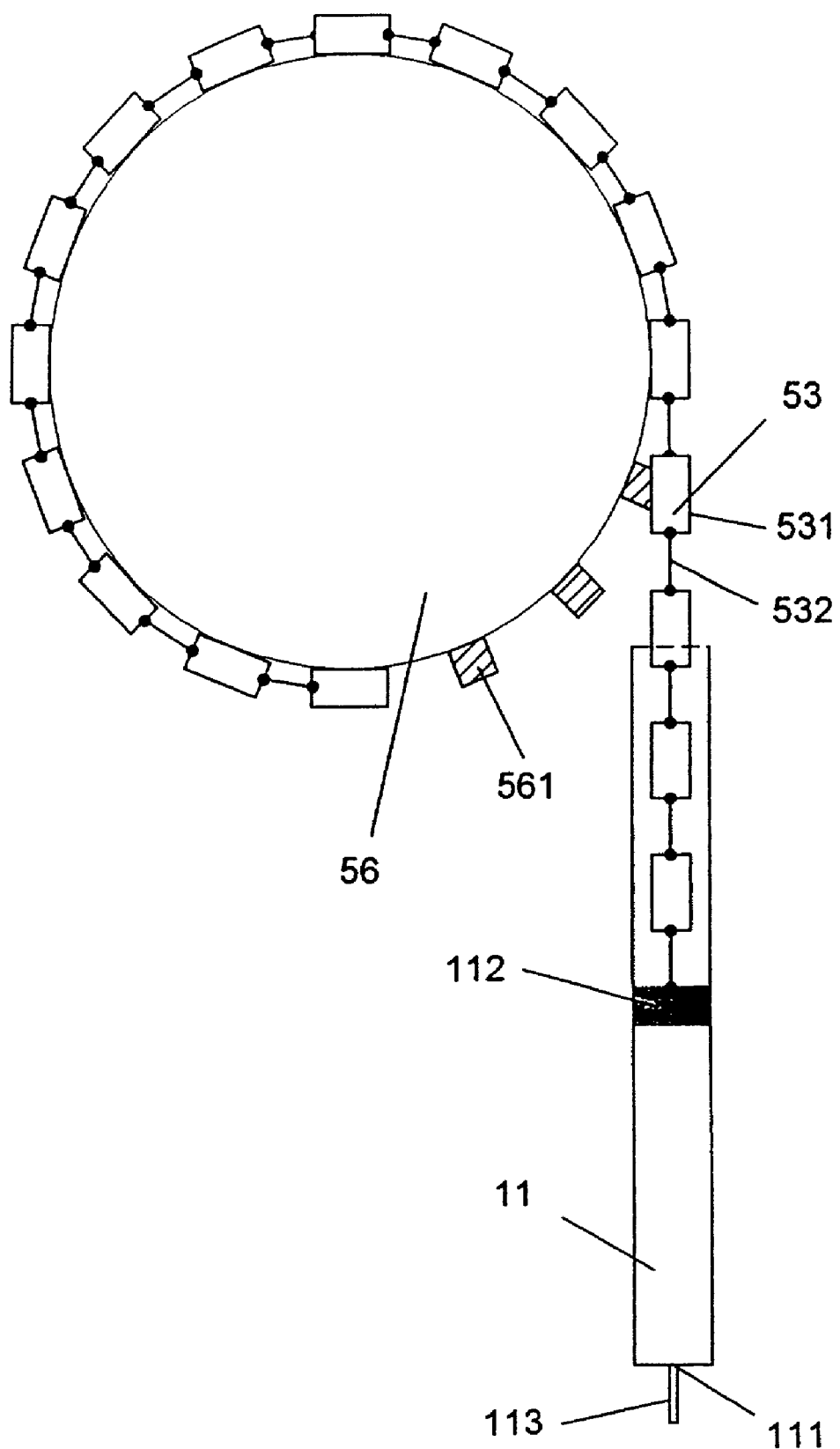
FIG. 5 shows a chain like piston rod and corresponding driving means according to the invention for which periodic as well as stochastic non-linearities may be present.

The figures are schematic and simplified for clarity, and they just show details which are essential to the understanding of the invention, while other details are left out.

DETAILED DESCRIPTION OF EMBODIMENTS

FIGS. 1.a and 1.b show the basic principles of a medication delivery system according to the invention.

A medication delivery system 1 is schematically shown in FIG. 1.a.

A cylindrical medication cartridge 11 (e.g. a replaceable one) comprising a piston 112 at one end and an outlet 111 at its opposite end is shown in its operational position to be fixedly held relative to an electromotor 15 for actuating the movement of the piston 112 by (schematically indicated) holding means 12. A needle 113 for leading a dose of medication from the cartridge to a body is connected to the outlet 111 of the cartridge 11.

The piston 123 has an inner 1121 and an outer surface 1122. The inner surface 1121 is in contact with the liquid medication contained in the cartridge 11. The outer surface 1122 is adapted to engage with one end 136 of the piston rod 13.

A piston rod 13 is shown to be operable to engage and displace the piston 112. The piston rod cooperates with driving means 161, 162 to transfer the angular movement (as indicated by arrows 150) of the electromotor 15 to a linear displacement (as indicated by arrows 130) of the piston rod 13. The piston rod 13 in FIG. 1.a is mainly cylindrical, axially stiff, and provided with threads (not shown) that, together with a corresponding driving nut 162 (fixedly held in an axial direction of the piston rod by holding means 163) provided with a gear wheel (not shown) on its outer periphery and a corresponding cooperating gear wheel 161 on the motor, constitute the driving means for converting movement from the motor 15 to the piston rod 13. The piston rod 13 is prevented from rotating about its longitudinal axis by holding means 134 that are adapted to follow the axial movement of the rod. In the embodiment in FIG. 1.a, the piston rod is assumed to have a longitudinal axis of rotational symmetry. This need, of course, not be the case. The piston rod may take any convenient form, cf. e.g. FIGS. 3-5 and our copending patent application "Medication delivery device with bended piston rod".

The medication delivery system consists of a replaceable part, comprising the medication cartridge (including the piston), a needle and possibly the piston rod, and a fixed part comprising the remaining parts of the system.

The movement 150 of the electromotor 15 is illustrated in FIG. 1.a by the circle 155 and the circular section 151 corresponding to an actual movement of the electromotor from a minimum or start position $D_{am,\,min}$ of the electromotor to the position $D_{am}(1)$ i.e. corresponding to a certain fraction of a turn (or a rational number of turns). A corresponding movement of the piston rod 13 is indicated by arrows 132 and 131 illustrating a movement of the piston rod from a minimum or start position $D_{p,min}$ to the position $D_p(1)$ corresponding to a specific dose $V_d(1)$. In FIG. 1.a. a movement of the electromotor and the piston rod from their respective start positions is indicated. The movement may of course commence at any instance within the operational range between the minimum and maximum positions $[D_{am,\,min};\,D_{am,\,max}]$ and $[D_{p,\,min};\,D_{p,\,max}]$, respectively.

The movement of the electromotor (and hence the piston rod) is controlled by a processing circuit, e.g. a micro processor 18. The processor has access to a memory 17 (either as a separate unit or as an integral part of the processor). Prior to the use of the medication delivery system 1, data 19 describing the actual movement 130 of the piston rod 13 as a function of the movement 150 of the electromotor 15 are loaded into a non-volatile part of the memory 17.

A battery 14 supplies electric energy to the electromotor 15, the processor 18 and the memory 17 (and to any other relevant parts of the system) via conductors 141.

The data 19 describing the actual movement 130 of the piston rod 13 as a function of the movement 150 of the electromotor 15 may be loaded in the form of an algebraic function $D_p = f(D_{am})$ (if at hand) describing corresponding values of angular position $D_{am}$ of the electromotor and linear position $D_p$ of the end 136 of the piston rod 13 engaging the piston 112 at its outer surface 1122. Alternatively, data 19 may consist of a table of corresponding values of $D_{am}$ and $D_p$ over the operating range of the device with an appropriate density of data (e.g. 100 values per turn of the motor). In a preferred embodiment the data 19 are obtained by a calibration procedure, optionally carried out during the production and configuration of the medication delivery system, preceding the normal use of the device.

A very simple example of inaccuracies that influence the ejected dose in an injection device is the case of a threaded piston rod that is driven by a corresponding nut. If, e.g., the thread is specified to a pitch of 0.70 mm per turn+−0.05 mm and if the extreme case of the thread per turn is 0.75 mm constantly over the whole operational range of the rod is assumed, the deviation between actual dose and intended dose would reflect a corresponding inaccuracy, i.e. resulting in a constant relative overdose of approximately 7% (assuming that this tolerance is the decisive parameter in deciding the dose accuracy).

The table below illustrates an example of expected $D_{ep}$ and actual $D_p$ values of displacement of the piston rod 13 as a function of the rational number of turns $D_{am}$ of the actuating means 15. In the example a linear relationship between expected piston rod displacement $D_{ep}$ and the rational number of turns $D_{am}$ of the actuating means is anticipated. The deviation of the actual displacement $D_p$ therefrom (denoted 'LD error' in the table) has a stochastic character.

| AD[1] $D_{am}$ [turns] | Expected LD[2] $D_{ep}$ [mm] | Actual LD[2] $D_p$ [mm] | LD[2] Error [mm] | Dose[3] $V_d$ [IU] | Dose error[3] $V_d$ [IU] |
|---|---|---|---|---|---|
| 0 | 0 | 0 | 0 | 0 | 0 |
| 0.5 | 0.35 | 0.34 | −0.01 | 2.43 | −0.07 |
| 1 | 0.70 | 0.75 | 0.05 | 5.33 | 0.33 |
| 1.5 | 1.05 | 1.08 | 0.03 | 7.71 | 0.21 |
| 2 | 1.40 | 1.40 | 0.00 | 10.00 | 0.00 |
| 2.5 | 1.75 | 1.72 | −0.03 | 12.29 | −0.21 |
| 3 | 2.10 | 2.14 | 0.04 | 15.29 | 0.29 |
| 3.5 | 2.45 | 2.44 | −0.01 | 17.43 | −0.07 |
| 4 | 2.80 | 2.71 | −0.09 | 19.36 | −0.64 |
| — | — | — | — | — | — |
| $D_{am,max}$ | [$D_{am,max}$*0.70] | — | — | — | — |

Note 1: AD = Angular Displacement. It is assumed that $D_{am} = D_{am,min} = 0$ corresponds to one end of the operating range of the piston rod ($D_p = 0$) and $D_{am,max}$ to the other ($D_p = D_{p,max}$).
Note 2: LD = Linear Displacement
Note 3: It is assumed that dose $V_d$ varies linearly with actual linear displacement of the piston and that an actual LD of 0.7 mm corresponds to a dose of 5 IU (IU = International Unit, 100 IU = 1 ml).

The density of measurement points may of course be as fine as wished by subdividing each turn into smaller fractions of a turn.

In the table above a linear relationship between the actual displacement of the piston and the dose volume $V_d$ is anticipated (nominally 1 turn corresponding to a displacement of 0.70 mm and a dose of 5 IU). This need not be the case, however. The expected relationship could be a known non-linear relationship and the compensation procedure could take care of deviations from this known non-linear relationship. The rightmost column of the table shows deviation from the expected dose (denoted 'dose error') as a function of the rational number of turns $D_{am}$ of the actuating means.

In general, fix points on the medication cartridge and the piston rod to which all measurements are referred, must be defined. In FIG. 1.a and in the table above, the displacement of the piston rod relative to the medication cartridge is calculated as the displacement of the end 136 of the piston rod 13 engaging with the outer surface 1122 of the piston 112 (denoted $D_p(1)$ or 131) relative to the end 115 of the cartridge opposite the outlet 111 (denoted $D_{p, min}$ or 132).

FIG. 1.b shows a graphical example of the relationship between the movement Dam 150 of the electro motor 15 and the expected $D_{ep}$ 20 and actual $D_p$ 21 displacement of the piston rod 15. The graphical representation includes the interval $[D_{am, min}, D_{am, max}]$ (152, 153) of the movement of the electromotor corresponding to the operating range $[D_{p, min}, D_{p, max}]$ (132, 133) of the piston rod. Corresponding values of the position $D_{am}(1)$ 151 of the electromotor relative to a start value ($D_{am, min}$) and the expected $D_{ep}(1)$ 231 and actual $D_p(1)$ 131 values of the displacement of the piston rod relative to a start value ($D_{p, min}$) for a given dose Vd(1) relative to a start value (0) are indicated.

In a preferred embodiment, calibration data corresponding to the table above are measured and stored for every individual piston rod and corresponding driving means (e.g. a driving nut) and actuating means in a test setup where driving means and actuating means are those of the final medication delivery device. Alternatively the test setup may apply driving means and actuating means equivalent to those of the final medication delivery device, if convenient. The data for a given piston rod and corresponding driving means are stored in the memory means of the relevant medication delivery device either directly during calibration or at a later stage, e.g. by storing the data in a relevant storage device together with data identifying the individual medication device in question (possibly together with corresponding data for other devices) for later retrieval and loading.

FIG. 2 shows a possible appearance of a medication delivery system (without a housing) according to the invention.

The embodiment in FIG. 2 comprises a partially curved piston rod 13 cooperating with driving means 16 (in the form of a gear box) to transfer movement from the electromotor 15 to the piston rod 13. The electromotor is controlled by a processor 18 based on data stored in a memory 17, both electronic circuits being located on a printed circuit board (PCB) 22. The piston rod shows a 180 degrees bending to provide a compact device. The piston rod engages a piston (not shown) in the replaceable medication cartridge 11. The device delivers a specific dose to a user through an outlet 111 of the cartridge to which a replaceable needle (not shown) may be attached.

The dose is delivered by activating the electromotor 15 under control of the processing circuit 18 on the basis of prerecorded data stored in the memory 17. The dose may be preset in the device (e.g. by preloading such data in a memory) or based on a user input (through I/O means not shown, but which may e.g. take the form of a keypad and a display). A cap (not shown) to protect and optionally support the piston rod at its 180 degrees path and to cover the electromotor, PCB and other vital parts of the device is provided.

FIG. 2.a and 2.b show orthogonal plane views of the medication delivery system, whereas FIG. 2.c presents a perspective view of the system.

FIGS. 3.a, 3.b and 3.c show a tape-shaped piston rod and corresponding driving means according to the invention for which periodic as well as stochastic non-linearities may be present.

The piston 33 comprises a tape with centrally situated, regularly spaced circular holes 331 adapted to cooperate with corresponding protruding circular cylindrical members 361 on the driving drum 36. The driving drum is activated by an electromotor through appropriate driving means (e.g. a gear box). The holes are shown to be positioned along a centerline of the tape, but may of course be located at one or both longitudinal edges of the tape or along a line off the center line or in any other convenient way as long as the protruding means on the driving drum follow a corresponding pattern. Likewise the individual holes and corresponding protruding members may take on any convenient form, e.g. edged as opposed to circular, as long as the holes in the tape and the protruding members on the driving drum correspond.

FIG. 3.a and 3.b show orthogonal plane views of the piston rod and driving drum, whereas FIG. 3.c shows a perspective view of a coiled piston rod.

In FIGS. 3.a-3.c, the driving means on the piston rod and driving drum are shown as individual holes and corresponding protruding members, respectively. They might of course take on any other appropriate form, e.g. corresponding indentations or grooves and projecting members. Likewise, the receiving members may be located on the driving drum and the corresponding protruding members on the piston rod, if convenient.

The non-linearities in the transfer of angular movement from the electromotor to linear movement of the piston rod may have several origins.

One source involved in the interaction between the driving drum and the piston rod is the built-in variations in the distance between adjacent holes in the tape and in the geometrical form of each individual hole due to production tolerances. These deviations from ideality have their counterpart in the corresponding features of the driving drum. Together these inaccuracies will result in a non-linear variation in the actual displacement of the piston rod with angular movement of the electromotor. The deviation from the expected displacement will be of a stochastic nature. Other contributions to non-linearity may e.g. come from the interaction of gear wheels, etc. These contributions may be partly stochastic in nature and partly periodic.

Another source of non-linearity has its origin in the construction of the piston rod. As appears from FIG. 3.c, the tape may be coiled on the driving drum. Depending on the thickness of the tape and the diameter of the drum, the length of tape provided by each turn of the driving drum will decrease the fewer the number of times that the tape is coiled on the driving drum, and vice versa. This source of non-linearity is predictable in principle, however, since it has a geometric origin. A mathematical expression including the geometrical dimensions of the tape and the drum may be set up.

Yet another source of non-linearity is a possible nonconcentric suspension of the driving wheel or drum, which result in a periodic non-linearity that may be compensated by the present invention.

The contributions to non-linearity in the transfer of angular movement from the electromotor to linear movement of the piston rod are thus partly of a stochastic nature and partly of a 'geometrical' nature. The latter may in principle be mathematically described and included in the correction algorithm of the processing unit. The former, however, can only be compensated for by a proper calibration of each individual device. Such a calibration will conveniently include all contributions 'automatically' (be they of a stochastic or geometric nature), so that a complete correction of the movement of the piston may be achieved on this basis. A limiting factor in the correction process is of course the accuracy with which the processing unit controls the angular movement of the electromotor.

If, however, the geometric contributions are dominating, a purely mathematical correction is of interest. In this case, a calibration of each unit prior to their (first) use is not necessary.

FIGS. 4.a and 4.b show a toothed piston rod and corresponding driving means according to the invention for which periodic well as stochastic non-linearities may be present.

FIGS. 4.a and 4.b illustrate only a part of a medication delivery system, namely the cartridge 11 with outlet 111 and piston 112, the latter being engaged with a serrated piston rod 43 comprising driving means 431 in the form of individual teeth placed beside each other in the length of the piston rod. A driving wheel 46 with individual teeth 461 adapted to cooperate with the teeth 431 of the piston rod 43 comprises another part of the driving means that are responsible for transferring the angular movement of the electromotor (not shown) to a linear displacement of the piston rod 43.

As discussed above for the tape-shaped piston rod of FIGS. 3.a-3.c, a contribution to the non-linearity in the transfer of angular movement from the electromotor to linear movement of the piston rod will have its origin in inaccuracies in piston rod and driving means due to production tolerances and possible other defects (e.g. due to mechanical damage) of these parts.

Another source, however, resulting in a cyclical and predictable contribution to the non-linearity, has its origin in the interaction of the teeth of the circular driving wheel and the teeth of the linear piston rod. The point of contact between a tooth of the driving wheel and a tooth of the piston rod will move during the 'cycle' of a given tooth of the driving wheel from its first contact with the actual tooth of the piston rod to its last contact with said tooth (before the next tooth of the driving wheel 'takes over'). This movement will give rise to a non-linear contribution to the movement of the piston rod with respect to the angular movement of the driving wheel (and thus the electromotor). A mathematical expression based on the geometrical dimensions of driving wheel and piston rod including the teeth on both may be set up and included in the correction algorithm. Alternatively, the combined effects of material inaccuracies and builtin geometrical non-linearities may be corrected for by making a calibration of each device prior to its (first) use.

FIG. 5 shows a chain-like piston rod and corresponding driving means according to the invention for which periodic as well as stochastic non-linearities may be present.

FIG. 5 again illustrates only a part of a medication delivery system, namely the cartridge 11 with outlet 111 (with needle 113) and piston 112, the latter being engaged with a 'chain-like' piston rod 53 comprising driving means in the form of individual links 531 placed beside each other in the length of the piston rod. Each link comprises a hole (not shown) and is connected to its neighbouring link by a connecting member 532. A driving wheel 56 with individual protruding members 561 adapted to cooperate with the holes of the links 531 of the piston rod 53 comprises another part of the driving means that are responsible for transferring the angular movement of the electromotor (not shown) to a linear displacement of the piston rod 53.

As discussed for the embodiments in FIGS. 3 and 4, the contribution to the non-linearity in the transfer of angular movement from the electromotor to linear movement of the piston rod is likewise composed of a stochastic part and a geometrical part. The geometrical part may in principle be compensated for by mathematical means and the combined effects of material inaccuracies and builtin geometrical non-linearities may be corrected for by making a calibration of each device prior to its (first) use.

Some preferred embodiments have been shown in the foregoing, but it should be stressed that the invention is not limited to these, but may be embodied in other ways within the subject-matter defined in the following claims. For example, the actuating means are exemplified as an angular electromotor. The actuating means could of course be any other convenient type including a linear motor.

The invention claimed is:

1. A method of configuring motorized injection device having a piston rod that pushes a piston in a medication cartridge to expel medication from the cartridge and having an actuator that drives the piston rod, the method comprising the steps of:
   a. calculating a relationship between movement of the actuator and expected movement of the piston rod;
   b. moving the actuator an amount expected to move the piston rod a predetermined distance;
   c. measuring the actual distance the piston rod moves when the actuator is moved in step b;
   d. determining the error between actual movement of the piston rod and expected movement when the actuator is moved a predetermined distance, wherein expected movement is a value calculated from design specifications and actual movement is a value measured from a calibration procedure;
   e. programming a processor to control the actuator to compensate for the error of step d so that the piston rod is moved by a desired amount even though the actuator is moved by a greater or lesser amount than would be expected to move the piston rod by the desired amount.

2. The method of claim 1, wherein steps a-d are repeated over a range of useable piston rod displacements and wherein the processor does not receive feedback from the device regarding piston rod movement.

3. The method of claim 2, wherein the prograninuing of the processor comprises first calculating an equation describing movement of the piston rod based on movement of the actuator.

4. The method of claim 3 wherein the equation is a linear equation.

5. The method of claim 3, wherein the equation is non-linear.

6. An apparatus for injecting a dose of medication, the apparatus comprising:
   a piston rod for expelling medication from a cartridge housed in the apparatus;
   an actuator that moves the piston rod by an amount necessary to expel a predetermined dose, wherein movement of the actuator by a given amount is expected to produce a given movement of the piston rod, but wherein actual movement of the actuator by a given amount does not result in the corresponding expected movement of the piston rod;
   a processor that is programmed to compensate for the difference between actual piston rod movement and expected actuator movement, the processor adapted to control the actuator to move the actuator an actual distance necessary to achieve the expected piston rod movement, wherein actual movement is a measured amount of displacement and wherein expected movement is the amount of movement calculated from design specifications.

7. A medication delivery device comprising a piston rod, an actuator that moves the piston rod, the movement of the actuator being expected to produce a given unit of movement of the piston rod for a given unit of actuator movement, a processor for controlling the actuator, and a data set comprising data indicative of actual actuator movement versus actual piston rod movement, the processor utilizing the data set to drive the actuator an actual distance necessary to produce a desired piston rod movement, wherein actual movement means the measurable movement that occurs and wherein expected movement refers to a calculated value for movement that should occur and which is calculated from design data.

8. A method of controlling the displacement of a piston rod in a processor controlled medication delivery device, wherein displacement of a piston rod within the device is directly related to the size of a dose of medication delivered by the device and wherein an actuator is used to move the piston rod, the method comprising the steps of:
   calculating the relationship between actuator movement and piston rod movement;
   creating a data set indicative of actual actuator movement versus actual piston rod displacement and storing that data in the processor;
   inputting a predetermined dose of medication to inject;
   calculating via the processor the actual distance the actuator must move to drive the piston rod a distance corresponding to the preset dose, wherein the calculating is done by applying the data set to compensate for difference between expected piston rod movement and actual piston rod movement, wherein actual movement is the actual measured distance the piston rod moves and expected movement is the distance that the rod would be expected to move and is calculated from design specifications.

9. A method of configuring a medication delivery device that comprises a piston rod, a piston rod drive, and an actuator, the method comprising the steps of:
   a. testing on a test set-up a plurality of piston rods, piston rod drives and actuators;
   b. storing data for each piston rod, piston rod drive, and actuator tested in step a, the data indicative of the actual movement of the actuator needed to drive the piston rod a predetermined distance, wherein actual movement corresponds to a measured value for the movement of the actuator;
   c. linking the stored data to the individual components;
   d. installing one of each component tested in step a into a medication delivery device;
   e. downloading the data for each of the components installed in step d into a processor in the delivery device, wherein the processor utilizes the data to control to drive the piston rod a predetermined distance corresponding to a user inputted dose to be delivered by the delivery device.

10. A method for delivering a medication from a drug delivery device that comprises a motorized actuator that drives a piston rod a distance wherein the distance the piston rod moves corresponds to the size of the dose delivered, the method comprising the steps of:
   collecting a first set of data that describes a relationship between actual movement of the actuating means and actual movement of the piston rod, wherein the first set of data is taken to mean a set corresponding to isolated values over a range or alternatively an algebraic expression valid in a range and wherein the first set of data is arrived at thru a prerecorded calibration procedure performed on the drug delivery device;
   calculating on a processor the movement of the actuator needed to expel a desired dose that is inputted by a user, wherein the calculation is performed by applying the data in the first data set to calculate actual movement of the actuator needed to deliver a set does,
   wherein the actual movement needed is different from the calculated movement for that the actuator that is calculated from design specifications for the actuator,
   wherein the first data set takes into account differences between a design specification for the actuator and error,
   utilizing the data in the first data set so that the actuator is sending a signal from a processor to the actuator to drive the actuator, wherein the signal is computed by the processor on the basis of a desired dose size that is inputted by a user and the first set of data.

11. A drug delivery device comprising:
   a motorized actuator;
   a piston rod drive by the actuator,
   a memory that stores a first set of data or an equation describing the relationship between actual movement of the actuator and actual movement of the piston rod,
   wherein the data is collected by performing a calibration procedure on the actuator and/or piston rod, wherein the actual movement is determined by making measurements and the expected movement is made by making calculations using design criteria for the actuator piston, rod, and related components; and
   a processor that, based on the first data set, sends a signal that causes the actuator to move an actual distance necessary to drive the piston rod a distance necessary to expel a user selected dose of a drug from the device.

* * * * *